United States Patent [19]

Singh et al.

[11] Patent Number: 5,516,903
[45] Date of Patent: May 14, 1996

[54] PROCESS FOR PREPARING [IR-(1α,2β-3α)]-2-AMINO-9-[2,3-BIS(HYDROXYMETHYL)CYCLOBUTYL]-1,9-DIHYDRO-6H-PURIN-6-ONE

[75] Inventors: Janak Singh; Gregory S. Bisacchi, both of Lawrenceville; Richard H. Mueller, Ringoes, all of N.J.

[73] Assignee: E. R. Squibb & Sons, Inc., Princeton, N.J.

[21] Appl. No.: 334,283

[22] Filed: Nov. 4, 1994

Related U.S. Application Data

[62] Division of Ser. No. 888,077, May 26, 1992, Pat. No. 5,412,134.

[51] Int. Cl.$^6$ .................................................. C07D 473/18
[52] U.S. Cl. ............................................ 544/264; 544/266
[58] Field of Search ........................................ 544/264, 266

[56] References Cited

U.S. PATENT DOCUMENTS

| | | | |
|---|---|---|---|
| 2,936,324 | 5/1960 | Haser et al. | 568/839 |
| 5,064,961 | 11/1991 | Bisacchi et al. | 556/436 |
| 5,126,345 | 6/1992 | Slusarchyk et al. | 556/443 |
| 5,153,352 | 10/1992 | Norbek et al. | 560/17 |
| 5,185,463 | 2/1993 | Godfrey et al. | 562/506 |
| 5,412,134 | 5/1995 | Singh et al. | |

FOREIGN PATENT DOCUMENTS

| | | |
|---|---|---|
| 335355 | 10/1989 | European Pat. Off. . |
| 358154 | 3/1990 | European Pat. Off. . |
| 366059 | 5/1990 | European Pat. Off. . |
| 452729 | 10/1991 | European Pat. Off. . |
| 458643 | 11/1991 | European Pat. Off. . |

OTHER PUBLICATIONS

Fieser et al., "Reagents For Organic Synthesis", vol. 2, 1972, p. 228.
Fieser et al., "Reagnets For Organic Synthesis", vol. 9, 1981, p. 486.
Fieser et al., "Reagents For Organic Synthesis", vol. 6, 1977, p. 307.

*Primary Examiner*—Johann Richter
*Assistant Examiner*—John Peabody
*Attorney, Agent, or Firm*—Stephen B. Davis

[57] ABSTRACT

The protected cyclobutanone of the formula

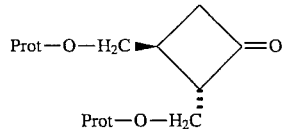

is treated with a dialkylaluminum chloride, an alkylaluminum dichloride, a trialkylaluminum compound, hydrogen in the presence of the catalysts ruthenium black or ruthenium on alumina, diphenyl-silane in the presence of tris(triphenylphosphine) rhodium (I) chloride, or iridium tetrachloride to yield the corresponding diprotected cyclobutanol. This compound is useful as an intermediate in the preparation of antiviral agents.

13 Claims, No Drawings

PROCESS FOR PREPARING [ IR-(1α ,2β -3α )] -2-AMINO-9-[ 2,3-BIS(HYDROXYMETHYL)CYCLOBUTYL] -1,9-DIHYDRO-6H-PURIN-6-ONE

This is a division of application Ser. No. 888,077, filed on May 26, 1992, now U.S. Pat. No. 5,412,134.

BACKGROUND OF THE INVENTION

Slusarchyk et al. in European Application 335,355 disclose that reduction of the diprotected (trans) cyclobutanone of the formula

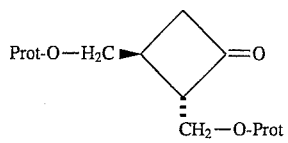

with sodium borohydride or sodium cyanoborohydride gives the racemic (1α, 2β, 3β) cyclobutanol of the formula

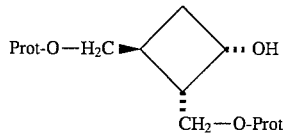

as the minor product which can then be converted an antiviral agent such as (±)-( 1α, 2β, 3α)-2-amino-9-[2,3-bis (hydroxymethyl) cyclobutyl]-1,9-dihydro-6H-purin-6-one.

Bisacchi et al. in U.S. Pat. No. 5,064,961 disclose preparing the optically active form of the purinyl antiviral agent of the formula

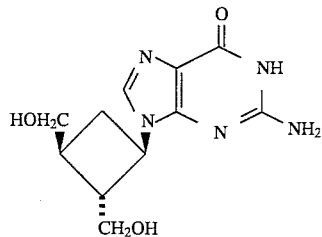

i.e. [1R-(1α, 2β, 3α)]-2-amino-9-[ 2,3-bis(hydroxymethyl) cyclobutyl ]-1,9 -dihydro-6H-purin-6 -one. Bisacchi et al. disclose preparing this antiviral agent from the intermediate

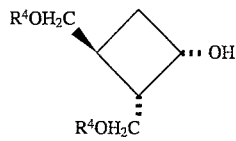

wherein $R^4$ is a protecting group such as a hindered silyl group, benzyl, substituted benzyl, aroyl, or acyl. Bisacchi et al. prepare this intermediate by treating the cyclobutanone

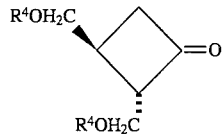

with a reducing agent such as hindered hydride reagents such as lithium tri-sec-butylborohydride, lithium trisiamyl- borohydride, diisobutylaluminum hydride and the like, preferably lithium trisiamylborohydride, and hindered borane reducing agents such as dicyclohexylborane, disiamylborane, and the like.

Norbeck et al. in European Patent Application 366,059 describe the preparation of this and related purinyl and pyrimidinyl antiviral agents by several routes. One disclosed process utilizes the conversion of the cyclobutanone

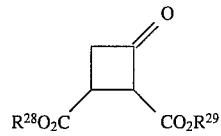

to the cyclobutanol

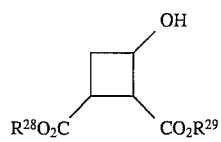

by treatment with a reducing agent such as sodium borohydride, sodium cyanoborohydride, or diisobutylaluminum hydride wherein $R^{28}$ and $R^{29}$ are lower alkyl, aryl, or arylalkyl, i.e., scheme XXIII C.

Ichikawa et al. in European Patent Application 358,154 also disclose the preparation of this and related purinyl and pyrimidinyl antiviral agents. Ichikawa et al. disclose that if the cyclobutanone

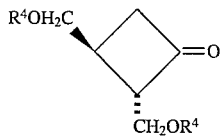

is reduced with a greatly sterically hindered reactant the 1,2-cis alcohol of the formula

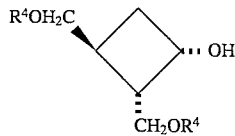

is preferentially formed. Examples of sterically hindered reactants are lithium tri (s-butyl) borohydride and di (isobutyl) aluminum hydride and $R^4$ is a protecting group such as t-butyldiphenylsilyl.

Pariza et al. in European Patent Application 452,729 and Ahmad in European Patent Application 458,643 disclose methods for preparing the optically active cyclobutanone

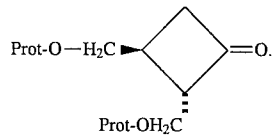

SUMMARY OF THE INVENTION

This invention relates to an improved process for the preparation of the diprotected 2,3-hydroxymethyl cyclobutanol of the formula

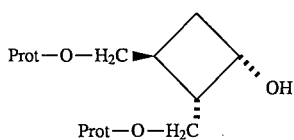

wherein Prot is a protecting group by treating the cyclobutanone of the formula

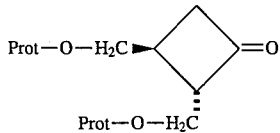

with a reducing agent selected from dialkylaluminum chlorides, alkylaluminum dichlorides, trialkylaluminum compounds, hydrogen in the presence of the catalysts ruthenium black or ruthenium on alumina, diphenylsilane in the presence of tris(triphenylphosphine)rhodium(I)chloride, and iridium tetrachloride in the presence of phosphorous acid to give the desired cyclobutanol of formula I in predominance to the undesired isomeric compound of the formula

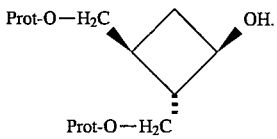 (III)

DETAILED DESCRIPTION OF THE INVENTION

The process of this invention can utilize the cyclobutanone of formula II in its optically active (2S-trans) form, also referred to as [2S,3S]. In this situation, the desired cyclobutanol of formula I will also be optically active, i.e., [1S-(1α, 2β, 3β)]. This optically active cyclobutanol can then be converted to an optically active antiviral agent such as [1R-(1α, 2β, 3α)]- 2-amino-9-[2,3-bis(hydroxymethyl)cyclobutyl]- 1,9-dihydro-6-H-purin-6-one.

The process of this invention can also utilize the cyclobutanone of formula II as the racemic compound in which situation the desired cyclobutanol of formula I will also be optically inactive, i.e., (1α, 2β, 3β). This racemic cyclobutanol can then be converted to an antiviral agent in racemic form such as (±)-(1α, 2β, 3α)- 2-amino-9-[2,3-bis(hydroxymethyl)cyclobutyl]- 1,9-dihydro-6H-purin-6-one.

In the diprotected 2,3-hydroxymethyl cyclobutanol of formula I, the relative stereochemistry of the substituents on the cyclobutyl ring are drawn to indicate that the hydroxy substituent is cis to the vicinal —CH$_2$—O-Prot substituent and that the two —CH$_2$—O-Prot substituents are trans to each other.

By treating the cyclobutanone of formula II with a reducing agent selected from dialkylaluminum chlorides such as diisobutylaluminum chloride, alkylaluminum dichlorides such as isobutylaluminum dichloride, trialkylaluminum compounds such as triisobutylaluminum, hydrogen in the presence of the catalysts ruthenium black or ruthenium on alumina, diphenylsilane in the presence of tris(triphenylphosphine)rhodium(I)chloride, and iridium tetrachloride in the presence of phosphorous acid, the desired diprotected 2,3hydroxymethyl cyclobutanol of formula I is obtained in predominance to the undesired isomeric compound of formula (III).

The term "alkyl" refers to straight or branched chain groups of 1 to 20 carbons, preferably 3 to 10 carbons.

Prot is a hydroxy protecting group. Suitable protecting groups include hindered silyl groups such as t-butyldimethylsilyl, t-butyldiphenylsilyl, (triphenylmethyl) dimethylsilyl, methyldiisopropylsilyl and triisopropylsilyl, suitable protecting groups also include substituted benzyl groups such as p-methoxybenzyl, and acyl groups of the formula

wherein R$_1$ is a straight or branched chain lower alkyl of 1 to 6 carbons, or phenyl, When the reducing agent employed in the process of this invention is a dialkylaluminum chloride suitable solvents for the reaction include unreactive aprotic solvents such as methylene chloride, toluene, and the like. The reaction can be run at a temperature of from about −90° C. to the boiling point of solvent, preferably at from about −90° C. to about 0° C., most preferably at about −40° C.

When the reducing agent employed in the process of this invention is an alkylaluminum dichloride such as isobutylaluminum dichloride or a trialkylaluminum compound such as triisobutylaluminum suitable solvents for the reaction include unreactive aprotic solvents such as methylene chloride, toluene and the like. The reaction can be run at a temperature of from about −90° C. to the boiling point of the solvent, preferably from about −90° C. to about 0° C. When the reducing agent employed is a trialkylaluminum compound then the protecting group Prot cannot be benzoyl.

When the reducing agent employed in the process of this invention is iridium tetrachloride in the presence of phosphorous acid, suitable solvents for the reaction include hydroxylic solvents such as water, methanol, propanol, isopropanol and the like or mixtures thereof such as water-isopropanol. The reaction can be run at a temperature of from about 50° C. to about 100° C., most preferably at about 80° C.

When the reducing agent employed in the process of this invention is hydrogen in the presence of the catalyst ruthenium black, suitable solvents for the reaction include hydroxylic solvents such as methanol, isopropanol, or mixtures thereof, preferably methanol. The reaction can be run at a temperature of from about −90° C. to the boiling point of the solvent, preferably at about 0° C. to about 50° C., most preferably at about 25° C.

When the reducing agent employed in the process of this invention is hydrogen in the presence of the catalyst ruthenium on alumina, suitable solvents for the reaction include hydroxylic solvents such as methanol, which is preferred, ethanol and the like but not isopropanol. The reaction can be run at a temperature of from about −90° C. to the boiling point of the solvent, preferably at 0° C. to 50° C., most preferably at about 25° C.

When the reducing agent employed in the process of this invention is diphenylsilane in the presence of tris(triphenylphosphine)rhodium (I) chloride, suitable solvents for the reaction include benzene, toluene, hexane, cyclohexane, and the like, preferably toluene or, alternatively, the reaction can be run in the absence of solvent. If the reaction is run in the presence of a solvent, then the reaction is carried out at a temperature of from about 0° C. to the boiling point of the solvent, preferably at about 25° C. If the reaction is performed without a solvent, then the reaction is carried out at a temperature from about 0° C. to about 120° C.

In the preferred process of this invention the reducing agent is a dialkylaluminum chloride, most preferably diisobutylaluminum chloride, the protecting group Prot is benzoyl, and the cyclobutanone starting material of formula II is in the optically active (2S-trans) form.

The optically active (2S-trans) diprotected 2,3-hydroxymethyl cyclobutanone of formula II can be prepared as described by Bisacchi et al. in U.S. Pat. No. 5,064,961, by Norbeck et al. in European Patent Application 366,059, by Ichikawa et al. in European Patent Application 358,154, by Pariza et al. in European Patent Application 452,729, or by Ahmad in European Patent Application 458,643. The racemic (trans)-diprotected 2,3-hydroxymethyl cyclobutanone of formula II can be prepared as described by Slusarchyk et al. in European Patent Application 335,355, as well, as in the European Patent Applications of Norbeck et al. and Ichikawa et al. mentioned above. Another method for preparing the optically active cyclobutanone of formula II is described by Godfrey et al. in U.S. patent application Ser. No. 770,191 filed Oct. 2, 1991.

As taught by Bisacchi et al. in U.S. Pat. No. 5,064,961 the optically active [1S-(1α, 2β, 3β)]diprotected 2,3-hydroxymethyl cyclobutanol of formula I can be treated with tosyl chloride to give the cyclobutane compound of the formula (IV)

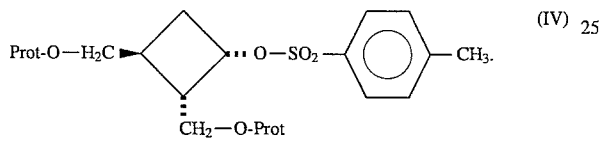

The tosyl compound of formula IV is then treated with the benzyloxy guanine of the formula (V)

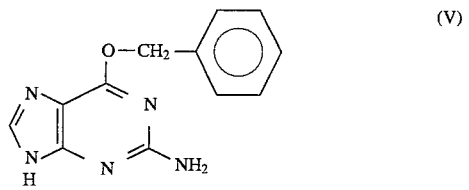

to give a compound of the formula (VI)

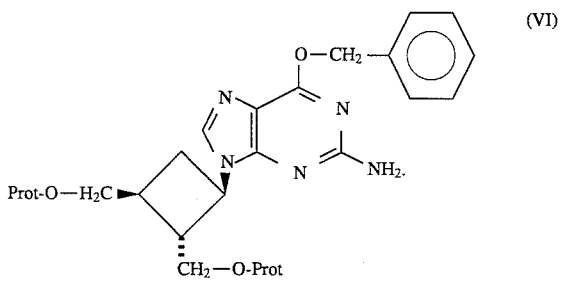

Removal of the protecting groups from the compound of formula VI yields the antiviral agent [1R-(1α, 2β, 3α)]-2-amino-9-[ 2,3-bis(hydroxymethyl)cyclobutyl ]-1,9-dihydro-6H-purin-6-one.

The following examples are illustrative of the process of this invention.

EXAMPLE 1

[1S-(1α, 2β, 3β)]-3-Hydroxy-1, 2-cyclobutanedimethanol, dibenzoate ester

A 3 1. three-necked flask equipped with a mechanical stirrer, an internal digital thermometer, an addition funnel, and nitrogen inlet was charged with 2385 ml. of anhydrous methylene chloride. After cooling to −40° C., diisobutylaluminum chloride (156.6 g., 886 mmole, 1.27 moleq.) was added. To this cold solution was added, dropwise via addition funnel over 63 minutes, a solution of (2S-trans)- 2,3-bis[(benzoyloxy)methyl]. Cyclobutanone (235 g., 699 mmole) in methylene chloride (600 ml.). The reaction was maintained at −40° C. for an additional 70 minutes. The reaction was quenched by the slow addition of methanol (502 ml.). During quench the temperature rose from about −40° C. to −32° C. over one hour. The cold bath was removed and a saturated aqueous solution of ammonium chloride (502 ml.) was added. After stirring for 18 hours, the mixture was filtered through anhydrous magnesium sulfate (502 g.) and the filter cake was washed thoroughly with methylene chloride. The filtrate was concentrated at reduced pressure and the residue was dried under pump vacuum at 35° C. to give 287.3 g. of crude product. The slightly wet solid was crystallized from about 2 l. of methanol and about 400 ml. of water to give 160.6 g. (yield 68%) of [1S-(1α, 2β, 3β)]-3-hydroxy-1,2-cyclobutanedimethanol, dibenzoate ester; m.p. 75°–77° C. TLC(silica gel; 40% ethyl acetate/ hexane) $R_f$=0.39. $[α]_D$=−15.3° (c=1.1, chloroform). HPLC:HI (215 nm, Zorabax-cyano column, water-acetonitrile gradient) 99.95%. Anal. calc'd. for: $C_{20}H_{20}O_5$ C, 70.38; H, 5.94; $H_2O$, 0.27 Found: C, 69.92; H, 5.87; $H_2O$, 0.27.

EXAMPLE 2

[1S-(1α, 2β, 3β)]-3 -Hydroxy-1,2-cyclobutanedimethanol, dibenzyl ether

A solution of (2S-trans) -2,3-bis [(benzyloxy)-methyl] cyclobutanone (0.5 g., 1.61 mmole) in toluene (1 ml. ) was added dropwise to a solution of isobutylaluminum dichloride (0.71 M in hexane, 3.41 ml., 2.42 mmole) at −78° C. The mixture was allowed to warm slowly to room temperature over 2 hours. After stirring for 30 minutes at room temperature, the mixture was allowed to stand at 0° C. overnight. After dilution with ethyl acetate, the reaction mixture was quenched with 10% hydrochloric acid. The organic phase was washed with brine, dried (magnesium sulfate) and the solvent evaporated to give [1S-(1α, 2β, 3β)]-3-hydroxy- 1,2-cyclobutanedimethanol, dibenzyl ether; TLC (50% ethyl acetate/hexane ) $R_f$=0.53.

EXAMPLE 3

[1S-(1α, 2β, 3β)]-3 -Hydroxy-1,2-cyclobutane-dimethanol, dibenzyl ether

A solution of (2S-trans) -2,3-bis [(benzyloxy) -methyl] cyclobutanone (0.2 g., 0.645 mmole) in toluene (4 ml.) was added dropwise over 10 minutes to a solution of triisobutylaluminum (0.91M in hexane, 0.9 ml., 0.816 mmole) in toluene (2 ml. ) at −40° C. The mixture was stirred at −50° C. for 4 hours and at −40° C for one hour. A solution of triisobutylaluminum (1 ml., 0.91 mmole) was added to the reaction mixture. After stirring for 30 minutes the reaction was quenched by adding 10% hydrochloric acid (2 ml.) at −40° C. The organic phase was washed with brine, dried (magnesium sulfate), and the solvent was evaporated to give [1S-(1α, 2β, 3β)]-3-hydroxy-2-cyclobutane-dimethanol, dibenzyl ether; TLC (30% ethyl acetate/hexane) $R_f$=0.3. The product contained about 5% of the isomeric compound; TLC (30% ethyl acetate/hexane) $R_f$=0.2.

EXAMPLE 4

[1S-(1α, 2β, 3β)]-3-Hydroxy-1,2-cyclobutanedimethanol, dibenzyl ether

A mixture of (2S-trans) -2,3-bis [(benzyloxy)-methyl] cyclobutanone (0.25 g., 0.806 mmole), iridium tetrachloride (0.016 g., 0.0483 mmole), phosphorous acid (0.397 g., 4.84 mmole) and water (0.3 ml.) in isopropanol (3 ml.) was refluxed overnight. The solvent was evaporated on a rotary evaporator. The residue was taken up in ethyl acetate and washed successively with 10% hydrochloric acid, brine, and 5% sodium bicarbonate. The organic layer was dried (magnesium sulfate) and the solvent was evaporated to give [1α, 2β, 3β)]-3-hydroxy-1,2-cyclobutane-dimethanol, dibenzyl ether; TLC (40% ethyl acetate/hexane) $R_f=0.51$.

EXAMPLE 5

(1α, 2β, 3β)-3-Hydroxy-1,2-cyclobutanedimethanol, dibenzoate ester

A suspension of ruthenium black (20 mg.) in isopropanol (1 ml.) was pre-hydrogenated under 1 atmosphere of hydrogen for one hour at room temperature. To this mixture, ( trans )- 2,3bis[(benzyloxy)methyl]cyclobutanone (200 mg.) in isopropanol (11 ml. ) was added and the combined mixture was stirred under 1 atmosphere of hydrogen at room temperature. After 21 hours, HPLC indicated the presence of (1α, 2β, 3β)-3-hydroxy-1,2-cyclobutanedimethanol, dibenzoate ester along with the isomeric compound (1α, 2α, 3β)-3-hydroxy-1,2-cyclobutanedimethanol, dibenzoate ester in a 84:16 ratio.

EXAMPLE 6

(1α, 2β, 3β) -3-Hydroxy-1,2-cyclobutanedimethanol, dibenzoate ester

A mixture of (trans)-2,3-bis [(benzoyloxy)-methyl] cyclobutanone (50 mg. ) and 5% ruthenium on alumina ( 10 mg.) in methanol ( 2 ml.) was stirred under 1 atmosphere of hydrogen at room temperature. After 46 hours, HPLC indicated the presence of (1α, 2β, 3β)-3-hydroxy-1,2-cyclobutanedimethanol, dibenzoate ester along with the isomeric compound (1α, 2β, 3α)-3-hydroxy-1,2 -cyclobutanedimethanol, dibenzoate ester in a 73:27 ratio.

EXAMPLE 7

(1α, 2β, 3β)-3-Hydroxy-1,2 -cyclobutanedimethanol, dibenzoate ester

Diphenylsilane (27.4 μl., 0.148 mmole) was added dropwise to a stirred solution of (trans)2,3 -bis [(benzoyloxy)methyl]cyclobutanone (50 mg., 0.148 mole) and tris-(triphenylphosphine)-rhodium (I) chloride (1.4 mg., 0.0015 mole) in toluene (0.75 ml. ) and kept for 15 minutes at room temperature under an argon atmosphere. The reaction mixture was then concentrated to an oil which was then stirred at room temperature for 1 hour with 10% aqueous methanol (1 ml.) containing a catalytic quantity of p-toluenesulfonic acid. The mixture was concentrated to an oil which was then partitioned between water and ethyl acetate. The ethyl acetate layer was washed with saturated aqueous sodium bicarbonate and brine, dried over anhydrous sodium sulfate, and the solvent removed to afford 55 mg. of a clear oil. HPLC of this oil indicated the presence of (1α, 2β, 3β)-3-hydroxy- 1,2cyclobutanedimethanol, dibenzoate ester along with the isomeric compound (1α, 2β, 3α)-3-hydroxy- 1,2-cyclobutanedimethanol, dibenzoate ester in along with cyclobutanedimethanol, dibenzoate ester in a 82:18 ratio.

What is claimed is:

1. A process for preparing the antiviral agent [1R-(1α, 2β, 3α])-2-amino-9-[2,3-bis(hydroxymethyl)cyclobutyl ]- 1,9-dihydro-6H-purin-6-one which comprises a) treating an optically active compound of the formula

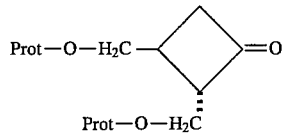

with a reducing agent selected from the group consisting of dialkylaluminum chlorides, alkylaluminum dichlorides, trialkylaluminum compounds, diphenylsilane in the presence of tris(triphenylphosphine) rhodium (I) chloride, and iridium tetrachloride in the presence of phosphorous acid wherein alkyl is straight or branched chain of 1 to 20 carbons; Prot is a hydroxy protecting group selected from the group consisting of benzyl, substituted benzyl,

t-butyldimethylsilyl, t-butyldiphenylsilyl, (triphenylmethyl) dimethylsilyl, methyldiisopropylsilyl, and triisopropylsilyl, and $R_1$ is straight or branched chain lower alkyl of 1 to 6 carbons or phenyl provided that when the reducing agent is a trialkylaluminum compound Prot cannot be

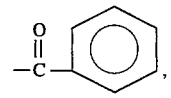

to give the optically active compound of the formula

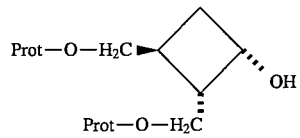

b) treating the product of step (a) with tosyl chloride to give the optically active compound of the formula

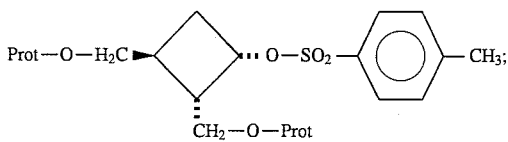

c) treating the product of step (b) with the benzyloxyguanine compound of the formula

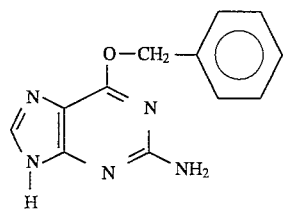

to give the optically active compound of the formula

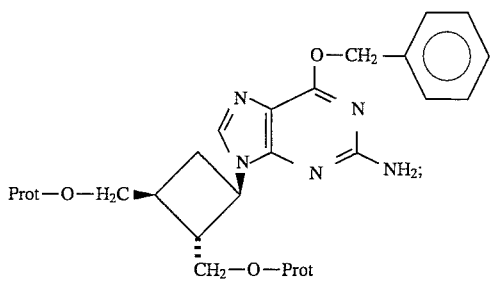

and d) treating the product of step (c) to remove the protecting groups and yield the desired antiviral agent.

2. A process of claim 1 wherein the reducing agent in step (a) is a dialkylaluminum chloride, the term alkyl refers to a straight or branched chain group of 3 to 10 carbons, and Prot is a hydroxy protecting group selected from the group consisting of benzyl, p-methoxybenzyl, benzoyl, t-butyldimethylsilyl, t-butyldiphenylsilyl,(triphenymethyl)dimethylsilyl, methyldiisopropylsilyl, and triisopropylsilyl.

3. A process of claim 1 wherein the reducing agent in step (a) is an alkylaluminum dichloride, the term alkyl refers to a straight or branched chain group of 3 to 10 carbons, and Prot is a hydroxy protecting group selected from the group consisting of benzyl, p-methoxybenzyl, benzoyl, t-butyldimethylsilyl, t-butyldiphenylsilyl, (triphenylmethyl)dimethylsilyl, methyldiisopropylsilyl, and triisopropylsilyl.

4. A process of claim 1 wherein the reducing agent in step (a) is a trialkyluminum compound, the term alkyl refers to a straight or branched chain group of 3 to 10 carbons, and Prot is a hydroxy protecting group selected from the group consisting of benzyl, p-methoxybenzyl, t-butyldimethylsilyl, t-butyldiphenylsilyl, (triphenylmethyl)dimethylsilyl, methyldiisopropylsilyl, and triisopropylsilyl.

5. A process of claim 1 wherein the reducing agent in step (a) is diphenylsilane in the presence of tris(triphenylphosphine) rhodium (I) chloride, Prot is a hydroxy protecting group selected from the group consisting of benzyl, p-methoxybenzyl, benzoyl, t-butyldimethylsilyl, t-butyldiphenylsilyl, (triphenylmethyl)dimethylsilyl, methyldiisopropylsilyl, and triisopropylsilyl, and the reaction in step (a) is performed in a solvent selected from the group consisting of benzene, toluene, hexane, and cyclohexane at a temperature of from about 0° C. to the boiling point of the solvent or the reaction in step (a) is performed in the absence of a solvent at a temperature of from about 0° C. to about 120° C.

6. A process of claim 1 wherein the reducing agent in step (a) is iridium tetrachloride in the presence of phosphorous acid, Prot is a hydroxy protecting group selected from the group consisting of benzyl, p-methoxybenzyl, benzoyl, t-butyldimethylsilyl, t-butyldiphenylsilyl, (triphenylmethyl) dimethylsilyl, methyldiisopropylsilyl, and triisopropylsilyl, and the reaction in step (a) is performed in the presence of a solvent selected from the group consisting of water, methanol, propanol, isopropanol, and mixtures thereof at a temperature of from about 50° C. to about 100° C.

7. A process of claim 2 wherein the reaction in step (a) is performed in the presence of an aprotic solvent selected from the group consisting of methylene chloride and toluene at a temperature of from about −90° C. to the boiling point of the solvent.

8. A process of claim 7 wherein the reducing in step (a) agent is diisobutylaluminum chloride and Prot is benzoyl.

9. The process of claim 8 wherein the reaction in step (a) is performed in methylene chloride at about −40° C.

10. A process of claim 3 wherein the reaction in step (a) is performed in the presence of an aprotic solvent selected from the group consisting of methylene chloride and toluene at a temperature of from about −90° C. to the boiling point of the solvent.

11. A process of claim 10 wherein the reducing agent in step (a) is isobutylaluminum dichloride.

12. A process of claim 4 wherein the reaction in step (a) is performed in the presence of an aprotic solvent selected from the group consisting of methylene chloride and toluene at a temperature of from about −90° C. to the boiling point of the solvent.

13. A process of claim 12 wherein the reducing agent in step (a) is triisobutylaluminum.

* * * * *